United States Patent [19]

Waterman

[11] Patent Number: 4,537,071
[45] Date of Patent: Aug. 27, 1985

[54] RETRIEVER TOOL
[75] Inventor: David K. Waterman, Placentia, Calif.
[73] Assignee: Rohrback Corporation, Seattle, Wash.
[21] Appl. No.: 554,317
[22] Filed: Nov. 23, 1983
[51] Int. Cl.³ .............................................. G01D 21/00
[52] U.S. Cl. .................................................. 73/432 R
[58] Field of Search .................. 73/432 B, 86, 863.85, 73/432 R; 137/317, 320

[56] References Cited
U.S. PATENT DOCUMENTS

| 980,665 | 1/1911 | Ord . | |
|---|---|---|---|
| 1,689,236 | 10/1928 | Fraser, Jr. . | |
| 1,730,305 | 10/1929 | Stancu, Jr. . | |
| 1,769,463 | 7/1930 | Rice . | |
| 2,217,216 | 10/1940 | Davis | 251/68 |
| 2,615,339 | 10/1952 | Holgersson et al. . | |
| 2,647,419 | 8/1953 | Dickason . | |
| 2,686,611 | 8/1954 | Burke . | |
| 2,746,470 | 5/1956 | Laird | 137/15 |
| 2,752,228 | 6/1956 | Gould . | |
| 2,770,532 | 11/1956 | Mason . | |
| 2,783,644 | 3/1957 | Willis | 73/86 |
| 2,870,629 | 1/1959 | Willis | 73/86 |
| 3,007,340 | 11/1961 | Kraftson | 73/432 |
| 3,031,742 | 5/1962 | Auer | 29/213 |
| 3,046,645 | 7/1962 | Smith | 29/240 |
| 3,174,332 | 3/1965 | Echtler, Jr. et al. | 73/86 |
| 3,822,718 | 7/1974 | Peterson | 137/317 |
| 3,865,129 | 2/1975 | Peterson | 137/315 |
| 3,995,655 | 12/1976 | Sands | 137/318 |
| 4,002,059 | 1/1977 | Jeffers et al. | 73/86 |
| 4,120,313 | 10/1978 | Lewis | 137/268 |
| 4,179,920 | 12/1979 | Schuller et al. | 73/86 |
| 4,215,458 | 8/1980 | Lancaster | 29/213 R |
| 4,275,592 | 6/1981 | Atwood et al. | 73/432 R |
| 4,294,124 | 10/1981 | Kalwaitis | 73/863.85 |
| 4,309,899 | 1/1982 | Torres | 73/86 |
| 4,327,586 | 5/1982 | Goddard | 73/432 B |
| 4,387,592 | 6/1983 | Welker | 73/432 B X |

FOREIGN PATENT DOCUMENTS 2758110 7/1979 Fed. Rep. of Germany .... 73/432 B
166543 10/1982 Japan ................................ 73/432 B Primary Examiner—Stewart J. Levy
Assistant Examiner—Tom Noland
Attorney, Agent, or Firm—Gausewitz, Carr, Rothenberg & Edwards

[57] ABSTRACT

A tool for retrieving or placing test or process elements from and into a pressurized container has a relatively short run in/run out shaft that carries a connector for attachment to and rotation of a holder that mounts a test probe, test coupon, or the like, in the container. The run in/run out shaft is driven by a pair of concentric drive cylinders, rotation of the shaft being achieved by a longitudinally slotted rotation drive cylinder, and longitudinal motion of the shaft being achieved by rotation of a spirally slotted cam cylinder. The arrangement provides a shorter length tool and eliminates gears and close-fitting drive elements that are subject to wear and damage from trash that may be contained in the fluid of the system.

27 Claims, 6 Drawing Figures

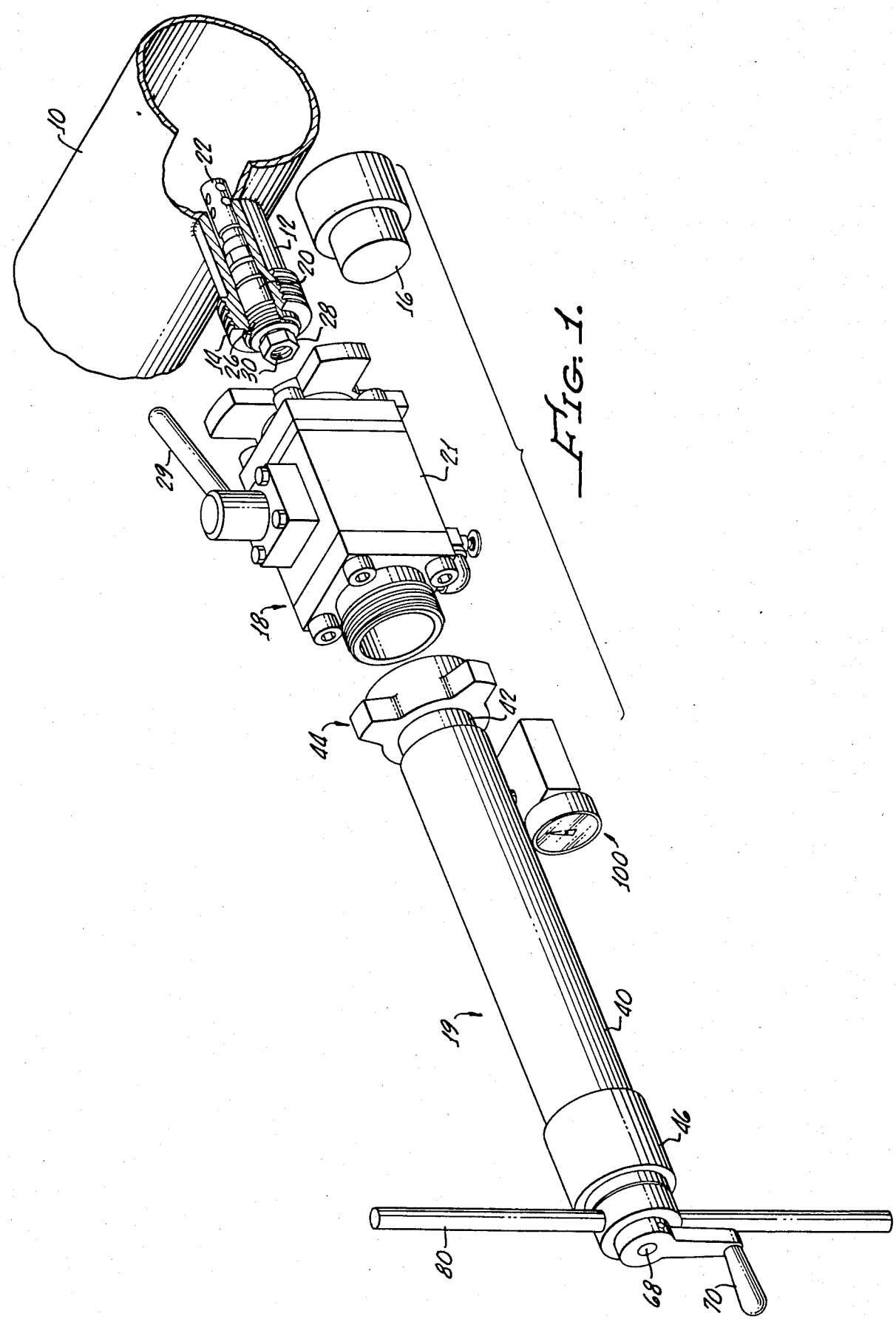

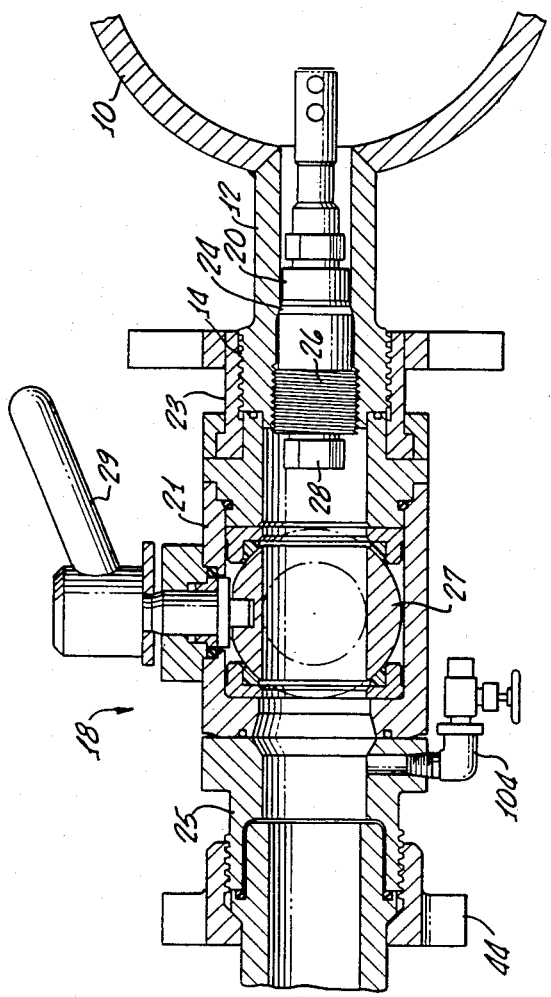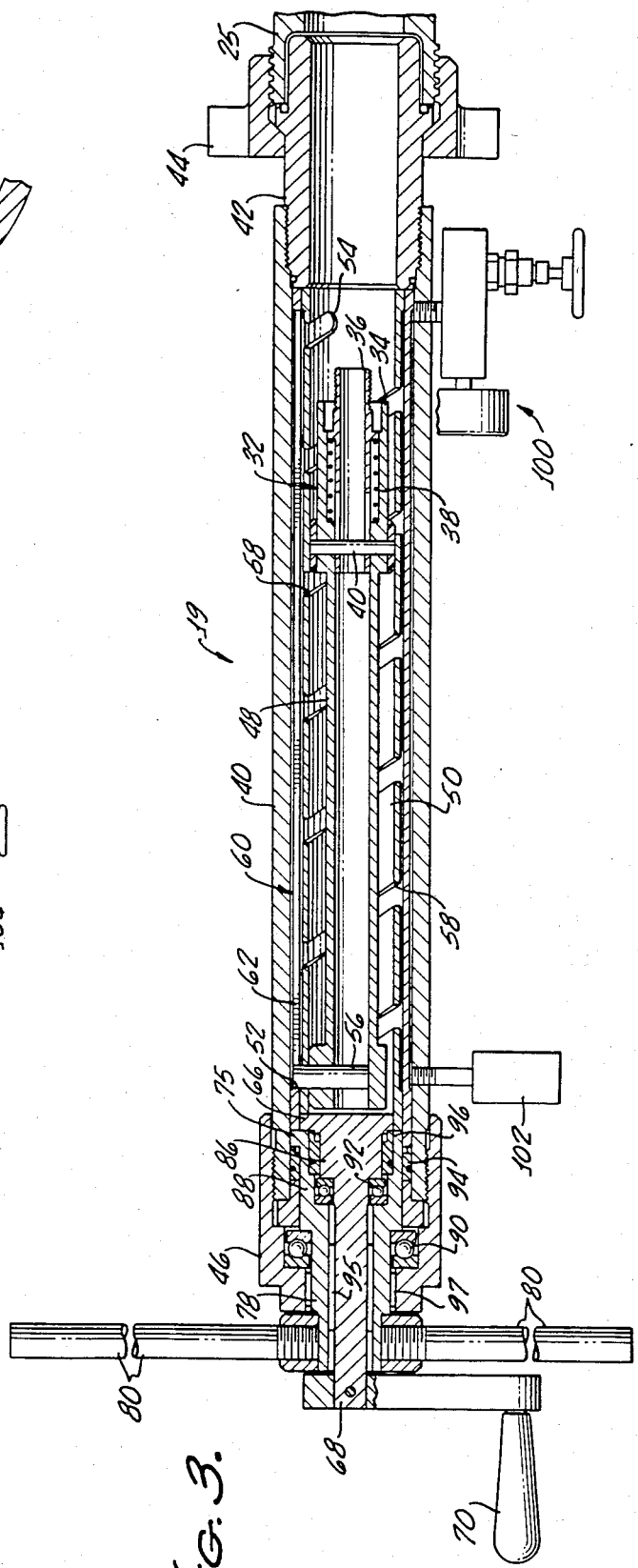

U.S. Patent Aug. 27, 1985 Sheet 3 of 3 4,537,071
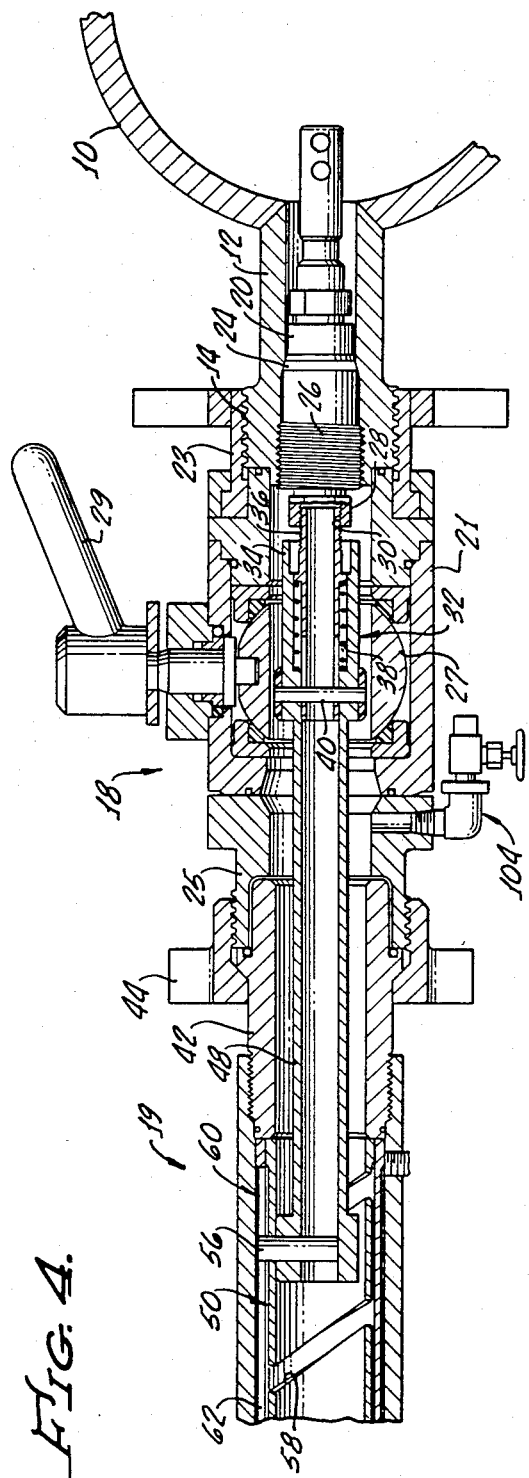
Fig. 4.
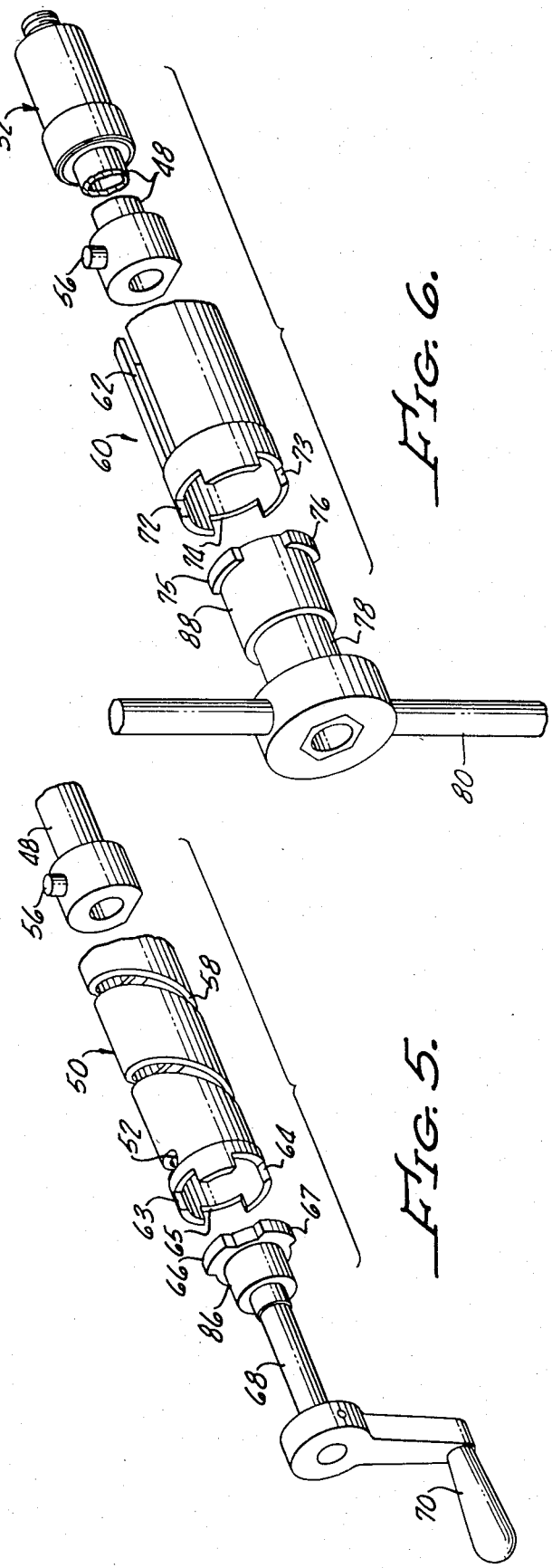
Fig. 6.
Fig. 5.

RETRIEVER TOOL

BACKGROUND OF THE INVENTION

The present invention relates to tools for retrieving and placing objects within a container, and more particularly relates to such a retriever tool for use when retrieving or mounting test or process elements such as corrosion or temperature probes, test coupons, anodes or the like.

In the processing and handling of fluids, such as for example transport or refining of oil and gas products, fluids often are confined and transported at high temperatures and exceedingly high pressures in closed containers or substantially closed transport systems. Monitoring and testing of the confined fluids, are frequently carried out by the insertion of corrosion monitoring probes, such as those known as the CORROSOMETER and CORRATER corrosion measuring probes, through fittings fixed to openings in the container or pipe walls. Test and processing probes include, among many others, not only corrosion measuring instruments, but temperature measuring instruments, corrosion coupons and anodes providing for cathodic protection. The test or monitoring devices, when inserted into the container, seal the opening and are frequently left in place for long periods of time. However, most have a limited life and must be removed and/or replaced periodically, preferably without shutting down or depressurizing the system being monitored.

Retriever tools developed for retrieving and installing such test or monitoring objects, generally include a pressure resistant housing in which is mounted a long transport shaft that carries a connecting device which is detachably coupled to the probe by suitable manipulation of the transport shaft. A valve is initially connected to the fitting in which the probe is installed, and the tool is connected to the valve in a pressure tight relation so that the valve may then be opened to allow access from the interior of the tool to the probe without loss of pressure, except to the interior of the tool. A transport shaft within the tool is then manipulated, driven forwardly and generally rotated, so as to grasp the probe and remove it from its threaded connection in the pipe access fitting.

A typical retriever tool is shown in U.S. Pat. No. 4,275,592 to Atwood et al., wherein the transport shaft is the form of a long rack which is driven longitudinally of the tool housing to extend through a valve into contact with a probe or coupon holder that is to be removed. Because the transport rack must extend from the tool and through a connecting valve and then be retracted into the closed and sealed body of the tool, the tool has a relatively great length. This length is a major disadvantage because space around the containers and pipes is frequently limited, particularly at points where probes and the like are inserted and positioned. Therefore in many instances it is difficult, if not impossible, to either place the access nipple at a most desired location or to provide access to the probe or the like by a tool of such length.

A devive such as that shown in the patent to Lancaster, U.S. Pat. No. 4,215,458, provides an arrangement where the tool has a decreased length but does so only at the expense of increased diameter and weight.

Retrieving tools of this general type, require at least two separate and independently controllable motions. The first is a run in or run out longitudinal motion which is employed to move the probe longitudinally of the tool, into position at the pipe or container or to remove it from its operating position. A second motion is a rotation of the probe connecting device to rotate the probe so that it may be threaded into and out of the threaded access nipple of the pipe.

The Atwood et al. U.S. Pat. No. 4,275,592 employs a second gear box having a worm and helical gear and a splined connection for effecting rotation. In order to obtain rotation, the arrangement of the patent to Lancaster, U.S. Pat. No. 4,215,458, employs a second shaft, parallel with the longitudinal screw drive, which is gear connected to rotate the longitudinally driven rod member to which the probe is to be connected. The Lancaster patent, like the Atwood el al. patent, involves relatively complex driving gears and gear boxes that are subject to wear and jamming in the presence of debris and other trash that is frequently carried into the tool during its use. Furthermore, the Lancaster arrangement, which actually requires three separate drive rods, inherently requires a larger tool diameter because of the need to accommodate side by side rods. Increased diameter introduces greatly increased forces in a high pressure tool. Wall thickness required to withstand the exceedingly high pressure involved becomes very great and the weight and cost of the tool are significantly increased. Further, the added tool weight and size makes the tool bulky and difficult to handle.

Accordingly, it is an object of the present invention to provide a retriever tool that avoids or minimizes these and other problems.

SUMMARY OF THE INVENTION

In carrying out principles of the present invention, in accordance with a preferred embodiment thereof, a retriever tool has an elongated drive means mounted in a housing which also mounts transport means to which is connected a connector for detachably securing a device to be retrieved. The transport means is mounted to the drive means for motion between a retracted position in which the transport means is retracted into overlapping relation with the drive means and an extended position in which the connector and part of the transport extend from the housing and from the drive means. According to a specific embodiment of the invention, the drive means is an elongated cam cylinder having a camming drive connection with a run in/run out shaft. No gears are employed for the drive thereby to significantly facilitate operation and life in the presence of debris and trash. Decreased tool length is achieved by the novel drive that allow use of a shorter run in/run out shaft having a connector that may be drawn into the housing in overlapping relation with respect to the longitudinal drive.

BRIEF DESCRIPTION OF THE DRAWINGS

FIG. 1 is an exploded perspective, with parts broken away, of the tool, a typical access valve and a typical fitting of a pipe having a probe installed therein.

FIG. 2 is a longitudinal section of the access fitting, valve and end of the tool.

FIG. 3 is a longitudinal sectional view of the tool.

FIG. 4 is a longitudinal sectional view of part of the tool, an access valve and an access fitting, showing a typical corrosion probe installed in a pipe.

FIG. 5 is an exploded perspective view of the longitudinal drive, showing portions of the slotted cam cylinder and run in/run out shaft.

FIG. 6 is an exploded perspective view of the rotational drive, showing portions of the longitudinally slotted drive cylinder and run in/run out shaft.

DETAILED DESCRIPTION

Referring to FIGS. 1, 2 and 4, a container such as a pipe 10 has an access fitting 12 welded to the periphery of a hole that extends through the pipe. The fitting has an external course thread 14 to which can be threadedly attached either a protective cover 16 or an access valve 18. Access fitting 12 is internally threaded for receiving a probe assembly having a probe holder portion 20 to which is secured a test instrument such as a probe 22. It will be readily understood that the probe is illustrated solely for purposes of explanation and that many types of devices may be attached to the holder 20 to be positioned as desired within the pipe 10. Such devices include CORRATER and CORROSOMETER corrosion measuring instruments, corrosion test coupons, temperature probes, anodes and other process control devices. The holder 20 seals itself to the fitting 12 at a sealing surface 24 (FIG. 4) as its external threaded portion 26 is threaded down into the internal threads of the fitting 12. A heavy duty protective cover 16 may be attached to the fitting 12 while the probe 22 is in use. The cover may be provided with an access hole for bringing cables out from the probe if deemed necessary or desirable. To facilitate insertion and retrieval of the probe holder 20, it is provided with a connector fitting having an hexagonal socket wrench receiving external surface 28 and an inner threaded bore 30.

A retriever tool, generally indicated at 19 in FIG. 1, is arranged to be threadedly connected to the access valve 18, so that by manipulating operating elements within the tool, the probe holder 20, together with the testing or processing object carried thereby, may be removed from the access fitting 12 and retracted into the body of the tool without releasing pressure within the pipe. For replacement and installation, the probe holder may be extended from the body of the tool and rotated into sealing engagement with the nipple 12. Access valve 18 is provided so that after retrieval and removal of the probe and probe holder, the valve 18 may be closed to seal the pipe. The access valve is conventional, comprising a housing 21, having threaded connections 23, 25 at opposite ends, and an apertured spherical valve closure 27 rotatable between valve open and closed positions by a handle 29. After installation of a probe and probe holder, which itself seals the access nipple 12, valve 18 may be removed. Thus only one valve and one tool need be provided for servicing of many access fittings and many probes or the like.

A probe connector 32 (FIGS. 3, 4) is provided as part of the tool and includes a device rotating torque tool in the form of a hex socket 34 that is adapted to be axially placed over the hex head 28 to enable rotation of the probe holder in and out of its threaded engagement with the nipple 12. In order to attach the probe holder to the connector 32 when it is disengaged from the nipple 12, connector 32 includes an axially shiftable externally threaded shaft 36 mounted within the socket 34 and spring pressed forwardly by a spring 38 interposed between a forward shoulder on the threaded shaft 36 and a rearward shoulder on the socket. A pin 40, fixed to the rear of the socket, extends through a pair of diametrically opposed longitudinal slots of threaded shaft 36 so that as the connector 32 is pressed forwardly (toward the right as seen in FIG. 4), abutment of threaded shaft 36 with the probe holder will drive threaded shaft 36 rearwardly (toward the left) and allow the socket 34 to engage the hex head 28. It will be understood that the illustrated connector 32 is merely exemplary of a number of different type of connectors that may be employed. It is contemplated that other types of connectors, well known in the art, may be secured to the tool 19 and used therewith provided, however, that such connectors can be operated by a combination of longitudinal and rotational motions.

The retriever tool 19, made of a high strength steel, includes a hollow elongated circular cylindrical housing 40 having an adaptor 42 threadedly fixed to its forward end. The adaptor mounts a hammer type coupling 44 having internal threads for securing the tool to the access valve threads 25 or directly to the access fitting 12 if deemed necessary or desirable. A pressure containing rear end cap 46 is threaded on the rearward end of the tool housing 40. Mounted within the housing 40 is a run in/run out or transport shaft 48, having a length considerably less than that of the housing, and fixedly carrying at its forward end the connector 32 and holder driving socket 34. Concentric with and surrounding the transport shaft 48, is a rotational drive in the form of a spirally slotted cam cylinder 50 (FIG. 5) having a continuous spiral slot that runs from a point 52 just short of its left or innermost end to a point 54 just short of its forward end. A drive pin 56 fixed to the rear end of the transport shaft 48 extends radially outwardly from the shaft into camming engagement with the spiral cam slot 58 of slotted cam cylinder 50. A second drive cylinder 60 (FIG. 6), concentric with and surrounding both the transport shaft 48 and cam cylinder 50, has a straight slot 62 extending longitudinally from a point near its rearward end to a point just short of its forward end. Drive pin 56 extends through the slot in cam cylinder 50 into slot 62 of the rotation cylinder 60. At their forward ends drive cylinders 50 and 60 abut the rear end of adaptor 42, which retains these cylinders in position at the forward end of the tool.

The rear end of spirally slotted cam drive cylinder 50 is formed with a plurality of rearwardly facing circumferentially spaced drive recess 63, 64, 65 which respectively receive three mating drive dogs 66, 67, and a third dog (not shown, fixed to the end of a translation drive head 68, having a hand operating crank 70 secured thereto. Similarly, the rearmost end of rotational drive cylinder 60 is formed with a plurality of circumferentially spaced rearwardly facing drive recesses 72, 73, 74, that respectively receive three mating drive dogs, of which those illustrated at 75 and 76 are shown, that are fixed to the forward end of a rotary drive head 78 that is manually rotated by a T-handle 80. As can be seen in FIG. 3, rotary drive head 78 is hollow and receive translation drive head 68 which extends therethrough. Drive head 68 terminates in an enlarged forward hub 86 that is positioned within and concentric with an enlarged forward hub portion 88 of rotation drive head 78 to provide a compact arrangement of the two concentric drives of the concentric cylinders 50 and 60 which are both restrained against axial metion in the housing. Thrust bearings 90 and 92 are positioned respectively between the end cap 46 and the rotation drive head 78 and between the translation drive head 68 and the enlarged hub 88 of the rotation drive head.

Combination backup rings and pressure seals 94, 96 provide suitable sealing of the interior of the tool housing. Bushings 95, 97 are interposed between the two drive heads 68, 78 and between the latter and the housing end cap 46. Pressure within the tool housing may be monitored and/or bled off by means of a pressure gauge and bleeder valve 100 connected to a fitting at the forward end of the tool and a purge valve 102 is provided at the rearward end of the tool. Access valve 18 also is provided with a bleeder valve fitting 104.

OPERATION

Assume that it is desired to employ the described tool to remove a probe and probe holder previously installed in the pipe 10 as shown in FIGS. 1, 2 and 4. The protective cap 16, if any, is removed and access valve 18 is securely connected to fitting 12. Tool 19 is then securely connected, by means of hammer fitting 44, to the outward end of the valve 18 and the valve is opened. Crank 70 is rotated in a counterclockwise direction to thereby rotate cam cylinder 50 in a counterclockwise direction so that cam drive pin 56 is driven rearwardly by the cam slot 52 or further into the tool. This well ensure that the run in/run out shaft 48 is in its rearmost or retracted position. In this position, as can be seen in FIG. 3, connector 32 is also in retracted position and is positioned not only inwardly of the end of the tool but also inwardly of forward ends of both of the cylindrical drive cylinders 50 and 60. Now crank 70 is turned clockwise to rotate cam cylinder 50 and drive the transport shaft 48 outwardly through the open access valve towards its extended position until the threaded connector nipple 36 makes initial contact with the internally threaded end 30 of probe holder 20. At this time, the threaded nipple 36 is in its spring urged forward position and accordingly will contact the probe holder before there is any contact between the holder and the connector socket 34. This contact of the threaded nipple 36 with the probe holder can be felt by the operator as an increase in resistance to turning of the crank handle 70. Any further turning of the crank handle 70, tending to drive the shaft 48 further outwardly of the housing, would tend to drive the threaded connector nipple 36 rearwardly, compressing the spring 38 and thereby increasing the resistance to turning of the drive crank 70.

Having accomplished initial contact between the threaded nipple 36 and the outer end of the probe holder, the T-handle 80 is rotated in a clockwise direction to rotate drive cylinder 60 and thereby rotate the transport shaft and connector 32. This clockwise rotation will cause the connector nipple 36 to threadedly engage the internally threaded end of the holder and is continued until such threaded engagement is accomplished for about one and one half to three or four turns. FIG. 4 illustrates this position wherein the threaded connector nipple 36 has engaged the internal threads 30 of the holder but the transport shaft 48 has not been extended far enough to engage the hex socket 34 with the hex head 28. When the connector has been threaded a few turns into the holder, the crank handle 70 cannot be rotated in either direction because the holder cannot be moved longitudinally. If at the same time the T-handle 80 cannot be rotated readily, then it is known that the run in/run out shaft has been extended too far and that the hex head and sockets have been engaged. In such a case, the crank 70 is rotated counterclockwise to disengage the socket and hex head and then the T-handle 80 is rotated clockwise to screw the threaded nipple into the holder. When such threaded engagement is ensured, crank 70 is again rotated in a clockwise direction to drive the shaft 48 still further forwardly so as to cause the connector socket 34 to slide over the hex head 28 of the probe holder. If necessary, during this final portion of the forward motion of shaft 48, the T-handle 80 is rotated slightly in one direction or the other to ensure rotational alignment of the hex socket with the hex head. Engagement of the hex socket with the hex head is signaled to the operator by a significant resistance to rotation of the T-handle 80. The T-handle is now rotated in a counterclockwise direction such that the probe holder and probe are rotated and begin to back out from the threaded engagement thereof in the access fitting 12. As the mating sealing surfaces of the probe holder and access fitting are mutually displaced, pressure begins to leak from the pressurized pipe 10 and to build up within the valve and tool interior. This pressure is allowed to build up to its maximum within the tool interior, so as to facilitate the subsequent continued counterclockwise turning of the rotation shaft 60 by means of T-handle 80 so as to complete the threaded withdrawal of the holder from the access fitting. The pressure gauge reading enables the operator to be sure that there has been equalization of pressure within the tool housing to allow completion of the retrieval. Completion of the separation of the holder threads from the access fitting is determined by the operator when the crank handle 70 can rotate with relative ease to thereby axially withdraw the connector, probe and probe holder from the access fitting and through the valve, completely backing out the probe and probe holder until the connector 34 is backed into its retracted position well within the housing as shown in FIG. 3. The valve 18 is then closed and pressure is bled from the tool housing by valve 102, 104.

When rotating T-handle 80 to turn the probe holder and back it out of the access fitting 12, shaft 48 will move toward the left and in so doing will automatically cam the translation drive cam cylinder so as to effect a small amount of rotation of the cam cylinder. The cam cylinder rotation is readily observed by the operator as a rotation of the handle 70 and thus he knows that the plug holder is being backd out. There is no binding of the rotational drive of the cam cylinder in this arrangement because the shaft 48 may be readily driven axially and is not restrained by its connection with the cam cylinder. In certain prior arrangements, such as that shown in the patent to Lancaster U.S. Pat. No. 4,215,458, backing out of the holder which has a different thread pitch than the pitch of the screw drive, will cause binding of the screw drive threads and thus when one shaft is rotated to back out the holder, the longitudinal drive shaft must also be rotated to avoid binding. No such binding access in the present arrangement.

The total length of the tool housing, including adaptor 42, is made sufficient to ensure that the probe, when retracted into the housing by means of the connector 34 and the probe holder 20, will not extend significantly beyond the forward end of the housing so that the tool may be readily disconnected from the valve (after the valve has been closed to seal the pipe 12), without the possibility of inadvertent damage to a projecting portion of the probe. Of course, it is only necessary that the travel of the shaft 48 be sufficient to withdraw the free end of the probe beyond the rearmost point of the valve closure, or by an amount just sufficient to enable the valve to be closed without interference with the forward end of the probe. The minimum longitudinal travel of the transport shaft 48 is thus governed in part by the length of the probe and the probe holder with which it is to be used. This travel must enable the probe to move from the installed position to a position in which it clears the valve 19 so as to enable closing of the valve before removal of the tool.

A significant advantage of the described tool, deriving from the configuration of its transport shaft drive, is the fact that the attached connector 34 may be withdrawn into the housing so as to be positioned in overlapping relation with respect to the longitudinal and rotary drive shafts 50 and 60. This drive arrangement makes possible a considerably shorter tool than is possible with a rack type drive. Moreover, the tool is completely free of gear boxes and employs a threaded connection only for interengaging the connector 34 with the probe holder. Thus, trash and debris carried by fluid within pipe 10 will not abrade or damage slidable parts. Clearances in the slot and pin drives are relatively large and spaces within the various drive cylinders are adequate to allow debris and trash to be driven into such spaces without excessive grinding and abrading action. Such trash and debris have in the past been a significant factor in diminishing the life of tools of this nature, particularly because of the frequent placement of probes and other devices installed and retrieved by such a tool in locations of the container or pipe system where trash and debris is most likely to collect.

For installation of a probe, substantially the reverse operation takes place. The run in/run out shaft 48 will be driven forwardly to project slightly from the end of the tool by rotating crank 70 and to enable the new probe to be threaded upon the threaded end of connector nipple 36 by at least several turns. The probe is then retracted into the tool housing and the housing is connected to the outer connection of the access valve 18. The valve is then opened slowly to allow pressure to build up within the interior of the tool housing. When the access valve is open, the gauge is observed to verify increased pressure in the tool. After completion of the installation, pressure from the tool will be bled and the gauge will be monitored for a short period of time to determine if pressure again builds up. If so, then it is known that the newly installed holder does not properly seal and the holder is removed and installed again. For installation, crank handle 70 is turned in a clockwise direction to drive the run in/run out shaft forwardly toward its extended position. As the holder threads 26 land upon the internal threads of the access fitting 12, the operator feels a resistance to further turning of the crank 70 but nevertheless continues to turn the crank to drive the shaft 48 still further forwardly, thereby to retract the threaded nipple 36 against the action of spring 38 and to slide the hex socket over the hex head 28, turning the crank handle 80 in one direction or the other to a slight degree to ensure rotational alignment of the hex head and hex socket. With the hex socket engaged, the T-handle 80 is rotated in a clockwise direction to thereby employ the hex drive to rotate the probe holder and probe, threading the holder into the threads of the access nipple 12. To ensure that the hex socket is not lifted off the hex head, crank 70 is rotated by a small amount during this operation, to ensure forward motion of the run in/run out shaft 48 and connector 32 during the threading of the holder in the access fitting. When the holder has been driven home in the access fitting and the sealed at sealing surface 24 therein, crank 70 is turned in a counterclockwise direction to retract the connector socket 34 from the hex head 28 and then the T-handle 80 is turned in a counterclockwise direction to rotate the run in/run out shaft 48 and connector 32 and thereby disengage the threaded nipple 36 from the internal threads of the holder.

As the T-handle 80 is rotated to retract the threaded nipple 36 and to disengage it from the holder, crank 70 may be moved slowly in a counterclockwise direction to slowly retract the run in/run out shaft 48. Complete disengagement of the threaded nipple 36 from the holder is signaled by the ability of the operator to rapidly and freely rotate crank 70 in a counterclockwise direction to retract the shaft 48. The crank 70 is then rotated to fully retract the shaft 48 and connector. The pressure within the housing and valve is bled off through the bleeder valve. Pressure is monitored for a short time, and then the tool and valves may be disconnected from one another and removed from the access fitting.

For use with many types of devices, such as CORRATOR or CORROSOMETER corrosion probes, orientation of the probe within the pipe is not important. Probes of this type can operate in any orientation. In certain other devices, such as test coupons for example, it is preferred to provide a selected orientation to the coupon with respect to the pipe. For such an operation, a mark is previously positioned on a portion of the probe that is visible after it has been installed, and the probe holder is rotated in its threaded engagement in the access fitting by a small amount in one direction or the other to obtain the desired orientation. Alternatively, the probe may be mounted within the holder with a small amount of rotational adjustment and suitable sealing provided between the probe and the holder so that the probe, which is marked to provide a visual indication of its orientation, may have its orientation adjusted relative to its holder after it has been installed. It will be understood that where electrical leads are connected to the probe, such leads will be brought out from the probe, through the probe holder and through the threaded opening at the rear of the probe holder.

There has been described a retrieval and installation tool having a number of advantages. The tool is relatively short, being significantly shorter than rack type tools, and has a smaller diameter, thinner wall and lesser weight than screw type tools and plural side-by-side shafts. The tool is readily operated by one man who can control both translational and rotational motion of the probe holding connector. The tool is operable to insert or retrieve a probe or other object that is sealed in a pipe access fitting without shutting down the system of which the pipe is a part. The pressure may remain in the system and is contained by the tool as the old probe is removed and the new one inserted. The tool is safer to use in high pressure systems than many prior tools which may subject their operators to serious danger and harm. Such harm can occur if the plug or holder being removed from its sealing relation in a high pressure system, is finally detached before pressure is allowed to build up within the tool housing so as to equalize pressure on both sides of the holder. In a rack type device, such a blowout will rapidly drive the rack backward along the length of the tool, possibly through the end of the tool, whereas in the device described herein, the run in/run out shaft is securely confined within the tool housing and rapid retraction would result only in rapid rotation of the crank handle 70 when the longitudinal drive cylinder 50 is rotated by longitudinal motion of the run in/run out shaft.

It will be readily appreciated that the described tool may be modified in many respects without departing from principles of the invention. The innermost of the three concentric cylinders, which is the transport shaft in the illustrated arrangement, may be either hollow or solid. The rotation drive cylinder may be positioned inside the translation drive cylinder or the transport shaft may be positioned outside of and surrounding either one or both of the drive cylinders. The drive slots, such as slot 62, may be grooved and other configurations of rearward end sealing and bearing arrangements may be used.

The foregoing detailed description is to be clearly understood as given by way of illustration and example only, the spirit and scope of this invention being limited solely by the appended claims.

What is claimed is:

1. A tool for retrieving a device holder from and inserting it into a vessel having an access fitting and an access valve connected with the fitting, said tool comprising
   an elongated tool housing,
   a transport shaft mounted in said housing for translational and rotational motion,
   connector means carried by said shaft for detachably securing a device holder to said shaft,
   translation drive means for axially driving said shaft between an extended position in which the shaft and connector means project forwardly of said housing so as to extend through said access valve and said access fitting and a retracted position in which the shaft is withdrawn into said housing, said drive means including an end portion that overlaps at least a portion of said connector means within said housing when said shaft is in said retracted position, and
   rotation drive means for rotating said shaft.

2. The tool of claim 1 wherein said drive means comprises a spirally slotted cam cylinder a longitudinally slotted rotation cylinder and a drive pin interconnecting said cylinders and said shaft.

3. The tool of claim 1 wherein said rotation drive means and translation drive means are mutually independent, whereby the shaft may be independently driven axially and independently rotated.

4. The tool of claim 1 wherein said translation drive means comprises a cam drive cylinder and interengaging cam and cam follower means on said cylinder and shaft.

5. The tool of claim 1 wherein said translation drive means comprises a cam cylinder having a spiral slot and wherein said shaft includes a cam pin secured thereto and extending into said slot, and including means for rotating said cam cylinder and restraining it against axial motion.

6. The tool of claim 5 wherein said shaft and connector means together have a length less than the length of said cam cylinder, whereby said connector means is retracted inwardly of the end of said cam cylinder when the shaft is in said retracted position.

7. The tool of claim 1 wherein said rotation drive means comprises a rotation cylinder concentric with said shaft and having a longitudinally extending slot, a drive pin secured to the shaft and extending into said slot, and means on the tool for rotating said rotation cylinder and restraining it against axial motion.

8. A retriever tool comprising
   an elongated housing,
   elongated drive means mounted in said housing,
   transport means, and
   connector means secured to said transport means for detachably securing a device to be retrieved to said transport means,
   said transport means being mounted in said drive means for motion between a retracted position in which said connector means is retracted into overlapping relation with said drive means and an extended position in which said connector means and a portion of said transport means extend from said housing and from said drive means,
   said drive means including means for driving said transport means between said positions.

9. The tool of claim 8 wherein said drive means comprises a cam cylinder and cam means interconnecting said cylinder and transport means in driving relation.

10. The tool of claim 8 including second drive means mounted in said housing for rotating said transparent means and connector means.

11. The tool of claim 10 wherein said second drive means comprises a rotation drive cylinder having a longitudinal slot, and a drive member interconnecting said rotation drive cylinder and transport means in driving relation.

12. The retriever tool of claim 10 wherein said transport means is mounted within said second drive means, and wherein said transport means is retracted into said second drive means in said retracted position and extends from said second drive means in said extended position.

13. The retriever tool of claim 10 wherein said first mentioned and second drive means and said transport means respectively comprise three mutually concentric cylinders, said transport means being rotatable and axially shiftable relative to said first mentioned drive means and being axially shiftable but rotatably fixed with respect to said second drive means.

14. The retriever tool of claim 10 wherein said transport means comprises a run in/run out shaft, wherein said first mentioned drive means comprises a first drive cylinder concentric with said shaft and having a continuous inclined cam slot formed therein, wherein said second drive means comprises a second drive cylinder concentric with said shaft and having a longitudinal slot, and including a drive member extending from said run in/run out shaft and into the slots of both said drive cylinders.

15. The retriever tool of claim 14 wherein the length of each of said cylinders is substantially the same as the combined length of said shaft and connector, whereby said connector can be retracted into overlapping relation with said cylinders.

16. The retriever tool of claim 8 wherein said drive means comprises a longitudinal drive cylinder extending for at least a major portion of the length of said housing and having a forward end adjacent the forward end of said housing, and wherein said transport means comprises a driven shaft having a length less than the length of said drive cylinder whereby said transport means in retracted position has a forward end thereof positioned inwardly of the forward end of said drive cylinder and inwardly of the forward end of said housing.

17. The retriever tool of claim 8 wherein said drive means comprises a spirally slotted cylinder rotatably mounted in said housing, wherein said transport means comprises a driven shaft mounted within said cylinder and having a length less than the length of said cylinder, and further including a drive pin fixed to said driven shaft and extending into the slot of said cylinder.

18. The retriever tool of claim 8 wherein said connector means comprises a device rotating torque head fixed to the end of said transport means, a threaded connector nipple carried by the torque head for limited longitudinal motion, and means for urging said threaded nipple forwardly, and further including second drive means mounted in said housing for rotating said transport means.

19. A tool for retrieving a device holder from and placing it in a pressurized vessel, said tool comprising
an elongated housing,
first, second and third mutually concentric cylinders in said housing,
said first cylinder comprising a rotational drive cylinder mounted for rotation in said housing,
means on said housing for rotating said rotational drive cylinder,
said second cylinder comprising a longitudinal drive cylinder mounted for rotation in said housing,
means on said housing for rotating said longitudinal drive cylinder,
said third cylinder comprising a transport shaft mounted for rotation and longitudinal motion in said housing,
connector means secured to said transport shaft for detachably coupling to the shaft an object to be retrieved or placed,
means for connecting said transport shaft with said rotational drive cylinder for rotating the transport shaft in response to rotation of the rotational drive cylinder, and
means for connecting said transport shaft with said longitudinal drive cylinder for longitudinally driving the transport shaft in response to rotation of the longitudinal drive cylinder.

20. The tool of claim 19 wherein said transport shaft is mounted within said housing for motion between a retracted position wherein said connector means is positioned within said housing and an extended position wherein said connector means and a portion of said transport shaft extend beyond said housing.

21. The tool of claim 19 wherein said transport shaft has a length less than the length of said first and second drive cylinders, and wherein said transport shaft is mounted for motion between an extended position wherein the connector means and a portion of said transport shaft extend beyond said first and second cylinders and beyond said housing and a retracted position wherein said connector means is positioned inwardly of the forward end of said housing and inwardly of the forward ends of said first and second cylinders.

22. The tool of claim 19 wherein said first cylinder has a slot extending longitudinally for substantially the full length thereof and wherein said second cylinder has a continuous spiral cam slot extending for substantially the full length thereof, and including a drive pin secured to said third cylinder and captured in the slots of said first and second cylinders, whereby said transport shaft may be rotated by rotation of said first cylinder and may be axially driven by rotation of said second cylinder.

23. The tool of claim 19 wherein said transport shaft is positioned within said first and second cylinders and has a length less than said first and second cylinders whereby said shaft and said connector means may be completely retracted within said first and second cylinders.

24. A tool for retrieving a device holder from and placing it in a pressurized vessel, said tool comprising
an elongated housing,
first and second mutually concentric cylinders in said housing,
said first cylinder comprising a rotational drive cylinder mounted for rotation in said housing,
means on said housing for rotating said rotational drive cylinder,
said second cylinder comprising a transport shaft mounted for rotation and longitudinal motion in said housing.
connecting means secured to said transport shaft for detachably coupling to the shaft an object to be retrieved or placed,
means for connecting said transport shaft with said rotational drive cylinder for rotating the transport shaft in response to rotation of the rotational drive cylinder, and
means for longitudinally driving said transport shaft.

25. The tool of claim 24 wherein said means for connecting said shaft with said rotational drive cylinder comprises a slot formed in one of said cylinders and a drive pin fixed to the other of said cylinders and captured in said slot.

26. A tool for retrieving a device holder from and placing it in a pressurized vessel, said tool comprising
an elongated housing,
first and second mutually concentric cylinders in said housing,
said first cylinder comprising a longitudinal drive cylinder mounted for rotation in said housing,
means on said housing for rotating said longitudinal drive cylinder,
said second cylinder comprising a transport shaft mounted for rotation and longitudinal motion in said housing,
connecting means secured to said transport shaft for detachably coupling to the shaft an object to be retrieved or placed,
means for connecting said transport shaft with said longitudinal drive cylinder for longitudinally driving the transport shaft in response to rotation of the longitudinal drive cylinder, and
means for rotating said transport shaft.

27. The tool of claim 26 wherein said means for connecting said shaft with said drive cylinder comprises a slot formed in one of said cylinders and a drive pin fixed to the other of said cylinders and captured in said slot.

* * * * *

UNITED STATES PATENT AND TRADEMARK OFFICE
CERTIFICATE OF CORRECTION

PATENT NO.  :  4,537,071

DATED       :  Aug. 27, 1985

INVENTOR(S) :  David K. Waterman

It is certified that error appears in the above-identified patent and that said Letters Patent is hereby corrected as shown below:

Claim 10 (column 10, line 23), delete "transparent" and substitute therefor ---transport---.

Signed and Sealed this

Seventeenth Day of February, 1987

*Attest:*

DONALD J. QUIGG

*Attesting Officer*  *Commissioner of Patents and Trademarks*